(12) United States Patent
Kim et al.

(10) Patent No.: US 9,196,946 B2
(45) Date of Patent: Nov. 24, 2015

(54) RESONATOR AND BIOSENSOR SYSTEM INCLUDING THE SAME

(71) Applicant: Electronics and Telecommunications Research Institute, Daejeon (KR)

(72) Inventors: Yark Yeon Kim, Daejeon (KR); Han Young Yu, Daejeon (KR); Won Ick Jang, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 191 days.

(21) Appl. No.: 13/960,773

(22) Filed: Aug. 6, 2013

(65) Prior Publication Data

US 2014/0167783 A1    Jun. 19, 2014

(30) Foreign Application Priority Data

Dec. 18, 2012   (KR) .......................... 10-2012-0148683

(51) Int. Cl.
| | |
|---|---|
| G01N 22/00 | (2006.01) |
| H01P 7/10 | (2006.01) |
| G01R 33/12 | (2006.01) |
| G01N 27/74 | (2006.01) |
| H01P 7/08 | (2006.01) |

(52) U.S. Cl.
CPC ................ *H01P 7/10* (2013.01); *G01N 27/745* (2013.01); *G01R 33/1269* (2013.01); *H01P 7/082* (2013.01)

(58) Field of Classification Search
USPC .................................................. 324/633–646
See application file for complete search history.

(56) References Cited

U.S. PATENT DOCUMENTS

| | | | |
|---|---|---|---|
| 7,800,378 B2 * | 9/2010 | Peters et al. .................. | 324/636 |
| 2008/0079646 A1 * | 4/2008 | Stuart ............................ | 343/795 |
| 2011/0199273 A1 * | 8/2011 | Kim et al. ..................... | 343/753 |
| 2012/0074957 A1 * | 3/2012 | Schroeder ..................... | 324/636 |
| 2012/0280872 A1 * | 11/2012 | Werner et al. ................. | 343/753 |

* cited by examiner

*Primary Examiner* — Vincent Q Nguyen (57) ABSTRACT

A resonator includes a dielectric substrate, a conductor disposed over the dielectric substrate, and a high-dielectric pattern disposed between outer parts of the conductor. The conductor includes an arc part, which has a C shape, and the outer parts, which respectively extend outward from both ends of the arc part, such that the conductor has an omega shape as a whole. The high-dielectric pattern has a relative permittivity greater than a relative permittivity of the dielectric substrate. The resonator has a flat plate shape to increase a filling factor of a sample, thereby improving measurement sensitivity. Also, the resonator is miniaturized, and thus a biosensor system including the resonator is also miniaturized.

15 Claims, 7 Drawing Sheets

RESONATOR AND BIOSENSOR SYSTEM INCLUDING THE SAME

CROSS-REFERENCE TO RELATED APPLICATIONS

This U.S. non-provisional patent application claims priority under 35 U.S.C. §119 of Korean Patent Application No. 10-2012-0148683, filed on Dec. 18, 2012, the entire contents of which are hereby incorporated by reference.

BACKGROUND OF THE INVENTION

The present invention disclosed herein relates to a resonator and a biosensor system including the resonator.

Typically, existing biosensors may be divided into two categories in terms of their use scope: one is applied to detect a quantitative bio-signal, and the other one is applied to determine whether the specific substances exist or whether the specific reaction occurs. To improve the sensitivity or reaction sensitivity with respect to the biological specific substances, an indirect method has been used for measuring the specific substances or the reaction sensitivity, i.e., various light, electricity, and magnetic markers are combined to an antibody to measure the markers through reaction with the antibody coupled to the biosensor through the antigen.

In the case of the method using a light sensor, it is convenient in that the reaction can be directly seen through the naked eye. However, for more sensitive detection, large-scaled equipment is required. Also, in the case of the method for measuring electrical properties (impedances) by using gold nano particles, there is difficulty in that an accurate sensor for the biosensor should be manufactured.

Generally, there are three methods for a biosensor system using a magnetic bead as a marker. The first method is a method for measuring an inductance change of an air-core coil inductor. The second method is a method for very accurately measuring a magnetic moment of a magnetic bead by using a superconducting quantum interference device (SQUID) that is an existing accurate magnetic measuring system. The third method is a method using a giant magnetoresistance device. Among these, in consideration of the efficiency and the economic feasibility, the first method is deemed as the most effective method for measuring a change of a permeability of a magnetic bead. However, a reasonable precondition in which a magnetic moment of a superparamagnetic bead should be large may be the most important factor for accurately measuring the change of the permeability. Also, in addition to the above-described method, studies are processing in two aspects. In the first aspect, various bridge circuits are realized in design of the measurement circuit. Also, in the second aspect, a measurement frequency increases to a high frequency.

Recently, a system for measuring an inductance change by using a magnetic bead may be generally realized within a frequency region of about several ten kHz to about several ten MHz. Also, the sensitivity of the biosensor increases through the change of the permeability in a frequency region of about several GHz.

SUMMARY OF THE INVENTION

The present invention provides a resonator that is capable of high-sensitively measuring a small amount of sample.

The present invention also provides a biosensor system that is capable of high-sensitively measuring a biological sample.

Embodiments of the present invention provide resonators including a conductive pattern including at least one gap region.

In some embodiments, the conductive pattern may have an arc shape having the one gap region or two arc shapes, which are symmetrical to each other, respectively having two gap regions.

In other embodiments, the resonators may further include: a circular quartz tube contacting an outer side of the conductive pattern; a low-loss filler surrounding an outer wall of the quartz tube; and a microwave shielding film surrounding an outer wall of the low-loss filler.

In still other embodiments, the resonators may further include a bridge electrode adjacent to the gap region and disposed between the quartz tube and the low-loss filler.

In even other embodiments, the conductive pattern may have an omega shape comprising an arc part having one gap region and outer parts respectively extending outward from both ends of the arc part, wherein the resonators may further include: a dielectric substrate disposed below the conductive pattern; and a high-dielectric pattern disposed between the gap regions.

In yet other embodiments, the high-dielectric pattern may have a permittivity of about 10 or more.

In further embodiments, the dielectric substrate may have a permittivity less than that of the high-dielectric pattern.

In still further embodiments, the dielectric substrate may have a permittivity of about 6 or less.

In even further embodiments, the conductive pattern may have a thickness of about 100 μm or less.

In yet further embodiments, the resonators may have a flat plate shape and include a plurality of materials having different permittivites.

In other embodiments of the present invention, biosensor systems include: two electromagnets spaced apart from each other; a resonator disposed between the electromagnets to receive electrostatic fields from the electromagnets; a microwave bridge emitting microwave electric fields into the resonator; and a microwave detector detecting microwave energy reflected from the resonator, wherein the resonator may include a conductive pattern comprising at least one gap region.

In some embodiments, the biosensor systems may further include a sample holder disposed within the resonator; and a biological sample disposed in the sample holder, wherein the biological sample may include a magnetic bead.

In other embodiments, the sample holder may be filled with the biological sample.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals in the drawings refer to like elements throughout.

In the following description, the technical terms are used only for explain a specific exemplary embodiment while not limiting the present invention. The terms of a singular form may include plural forms unless referred to the contrary. The meaning of "comprise" and/or "comprising", "include" and/or "including" specifies a property, a region, a fixed number, a step, a process, an element and/or a component but does not exclude other properties, regions, fixed numbers, steps, processes, elements and/or components. It will be understood that when an element such as a layer, film, region, or substrate is referred to as being "on" another element, it can be directly on the other element or intervening elements may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. For example, etching area illustrated as a right angle may be rounded or a shape having a predetermined curvature. Areas exemplified in the drawings have general properties, and are used to illustrate a specific shape of a semiconductor package region. Thus, this should not be construed as limited to the scope of the present invention.

Hereinafter, it will be described about an exemplary embodiment of the present invention in conjunction with the accompanying drawings.

Figure 1:
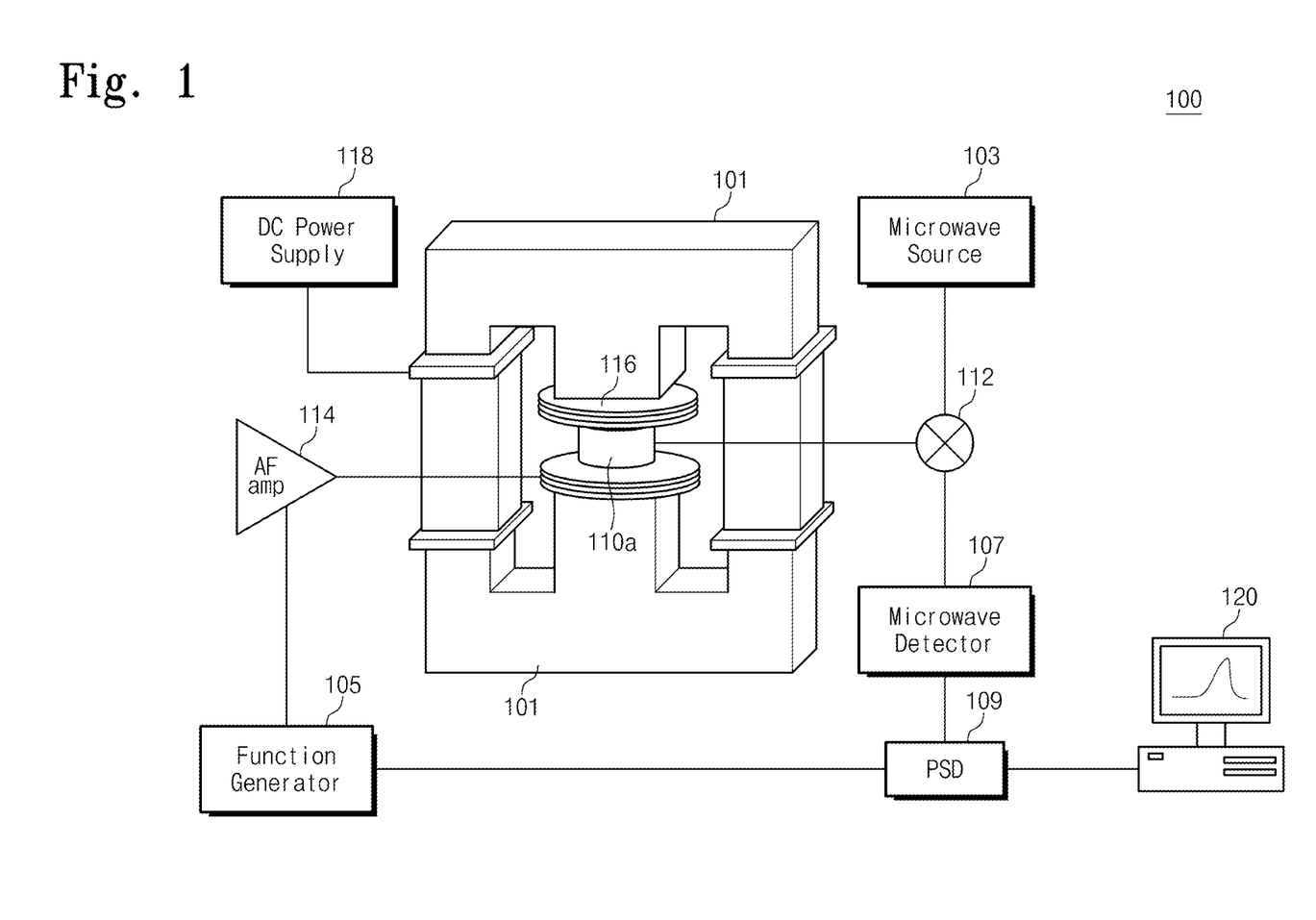
FIG. 1 is a view of a biosensor system according to an exemplary embodiment of the present invention.
Figure 2A:
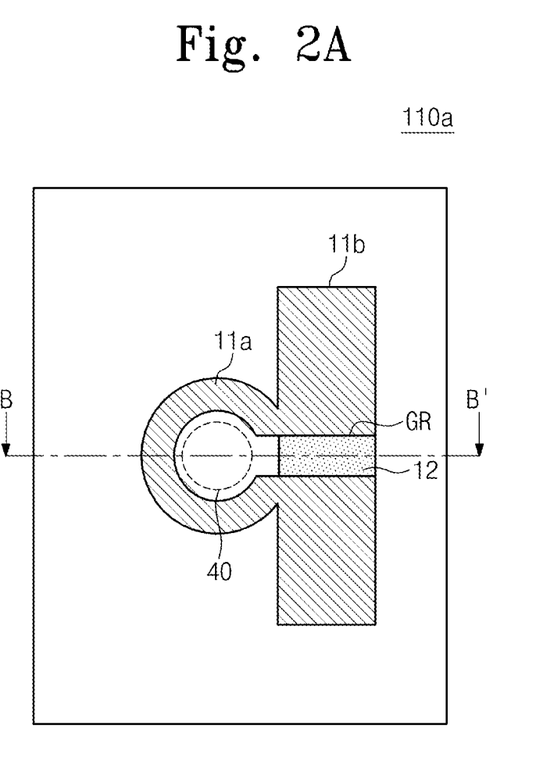
FIG. 2A is a plan view of a resonator according to an embodiment of the present invention.
Figure 2B:
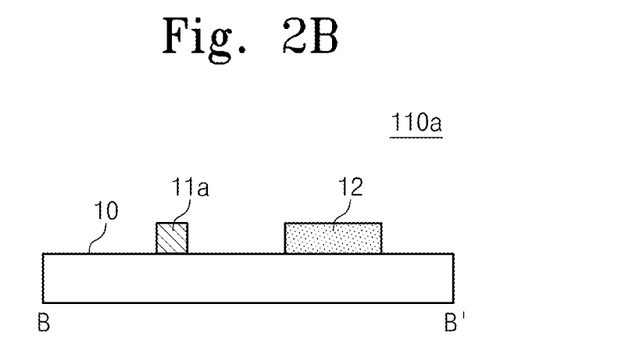
FIG. 2B is a cross-sectional view taken along line A-A' of FIG. 2A.
Figure 2C:
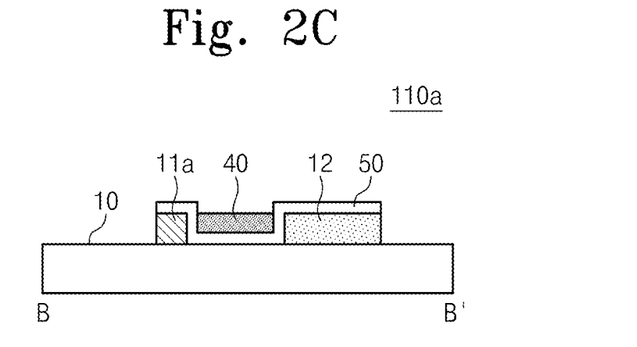
FIG. 2C is a cross-sectional view of a state in which the resonator is coupled to a sample holder according to the present invention.
Figure 3:
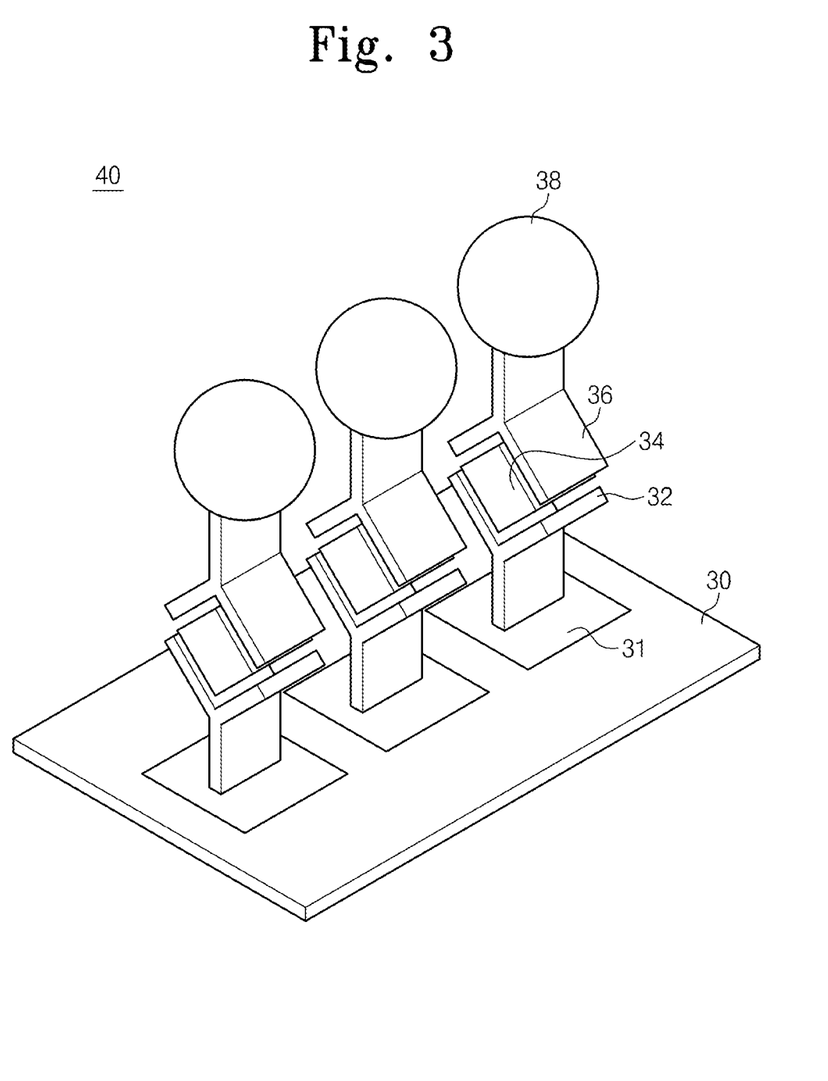
FIG. 3 is a view of a sample according to an exemplary embodiment of the present invention.

FIG. 1 is a view of a biosensor system according to an exemplary embodiment of the present invention. FIG. 2A is a plan view of a resonator according to an embodiment of the present invention. FIG. 2B is a cross-sectional view taken along line A-A' of FIG. 2A. FIG. 2C is a cross-sectional view of a state in which the resonator is coupled to a sample holder according to the present invention. FIG. 3 is a view of a sample according to an exemplary embodiment of the present invention.

Referring to FIGS. 1, 2A to 2C, and 3, a biosensor system 100 according to an exemplary embodiment of the present invention includes an electromagnet 101, a microwave source 103, a function generator 105, a microwave detector 107, a phase sensitive detector (PSD) 109, a resonator 110a, a microwave bridge 112, an AF amp 114, a Helmholtz coil 116, a DC power supply 118, and a signal analyzer 120. The electromagnet 101 may be an air-cooled type electromagnet. The DC power supply 118 may excite the electromagnet 101.

Referring to FIGS. 2A and 2B, a resonator 110a of an embodiment of the present invention may be a plate-type resonator manufactured in a microstrip technology. The resonator 110a may include a plurality of materials 10 and 12 having permittivities different from each other. Particularly, the resonator 110a includes conductive patterns 11a and 11b and a high-dielectric pattern 12 which are disposed on the dielectric substrate 10. The dielectric substrate 10 may have a permittivity less than that of the high-dielectric pattern 12. The dielectric substrate 10 may have a permittivity of about 6 or less. The conductive patterns 11a and 11b may include an arc part 11a having one gap region GR such as a C shape and outer parts 11b respectively extending outward from both ends of the arc part 11a. Thus, the conductive patterns 11a and 11b may have an omega shape on the whole. Each of the conductive patterns 11a and 11b may be formed of a metal such as gold, silver, brass, aluminum, or copper.

Each of the conductive patterns 11a and 11b may have a thickness of about 100 μm or less. The high-dielectric pattern 12 may be disposed in the gap region GR between the outer parts 11bs. The high-dielectric pattern 12 may have a permittivity of about 10 or more.

Referring FIGS. 2C and 3, a sample holder 50 may be inserted into an empty space of a center of the arc part 11a. The sample holder 50 may be formed of a nonmagnetic material having a low dielectric loss. The sample holder 50, for example, may be formed of glass or polydimethylsiloxane (PDMS). A sample 40 may be disposed within the sample holder 50. The sample holder 50 may be filled with the sample 40. The sample 40 may include a transducer 31 disposed on a sample substrate 30. Probe molecules may be provided in the transducer 31. A target molecule antigen 34, an antibody 36, and a magnetic bead 38 may be successively coupled to the probe molecules 31 through an antigen-antibody binding reaction. The sample 40 to be measured (hereinafter, referred to as a measurement sample) may receive a magnetostatic field of the electromagnet 101 and a microwave magnetic field which vertically cross each other. The measurement sample 40 may be a biological sample. The magnetic bead 38 within the sample 40 may align a magnetic moment in a direction of the magnetic field by the magnetostatic field and perform a precessional motion. The precessional motion may be changed in frequency according to a shape of the sample. For example, if the bead is magnetically isotropic and has a globular shape, the frequency of the precessional motion may increase in proportion to intensity of an external magnetostatic field.

Therefore, a microwave generated in the microwave generator 103 (or source) may be incident into the resonator 110 through the microwave bridge 112 (circulator) to generate a standing wave in the resonator 110. Also, when the microwave has the same frequency as that of the precessional motion, the resonance may occur to allow the sample to absorb microwave energy. Thus, a voltage generated in the microwave detector 107 for detecting the microwave energy reflected from the resonator 110a may decrease. To high-sensitively measure the microwave energy absorbed into the sample, a magnetic field modulation method in a frequency region of about 50 kHz to about 100 kHz may be used. As shown in FIG. 1, the magnetic field modulation may apply one output of the function generator 105 to the Helmholtz coil 116 near to the electromagnet through the AF amplifier 114 to supply an uniform magnetic field to the sample. Here, one output terminal of the function generator 105 is connected through the PSD 109. The PSD 109 may match a signal outputted from the microwave detector 107 with a phase of a reference frequency of the magnetic field modulation signal of the function generator 105 to output the signal in a differential form of a magnetic resonance absorption line. The signal may be analyzed by using the signal analyzer 120. The electromagnet 101 may be manufactured by using a transformer core (EI or C type) as shown in FIG. 1. Here, the intensity of the magnetic field may be controlled by using a hall device. Since the resonator 110a has a flat plate shape and a thickness which is not much thicker than that of the sample, a filling factor of the sample may increase to improve the measurement sensitivity. Also, since the dielectric substrate 10 has a permittivity different from that of the high-dielectric pattern 12, an electric field may be clearly separated from the magnetic field. That is, the microwave magnetic field may be maximized at the arc part 11a of the conductive pattern, but be minimized at the high-dielectric pattern part 12. Thus, since the sample 40 is disposed adjacent to the place where the electric field and the magnetic field are separated, the measurement sensitivity may be improved. Also, since the flat plate-type resonator is used, the resonator may relatively decrease in size, and thus, the electromagnet 101 may be designed with a small size. Therefore, the biosensor system may be miniaturized on the whole. Also, a portable biosensor system which measures the presence or absence of the magnetic bead to analyze specific substances or reaction of a body, thereby confirming the presence or absence of diseases may be realized. As a result, the biosensor system may be improved in sensitivity, efficiency, and convenience.

The resonator 110a may have a shape different from the flat plate shape. FIGS. 4A to 4D are plan views of a resonator according to exemplary embodiments the present invention. Resonators 110b to 110e may exclude the dielectric substrate 10.

Figure 4A:
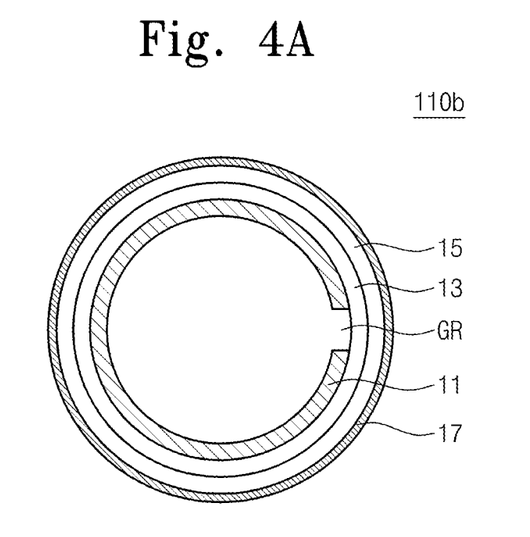
FIGS. 4A to 4D are plan views of a resonator according to exemplary embodiments the present invention.

Referring FIG. 4A, the resonator 110b of the current embodiment may include an arc-shaped conductive pattern 11 having one gap region GR, a circular quartz tube contacting an outer wall of the conductive pattern 11, a low-loss filler 15 surrounding the outer wall of the quartz tube 13, and a microwave shielding film 17 surrounding the outer wall of the low-loss filler 15. The shielding film 17 may be formed of a conductor having superior conductivity. For example, the shielding film 17 may be formed of at least one of copper, gold, and silver. The filler 15 may prevent the quartz tube 13 from being broken. The filler 15 may be formed of a nonmetallic material to prevent the modulation signal applied from outside from being lost.

Figure 4B:
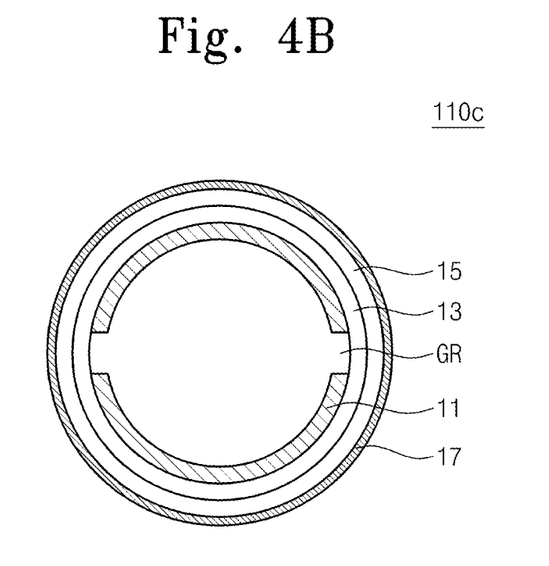

Referring to FIG. 4B, the resonator 110c of the current embodiment may have the same configuration as the resonator 110b of FIG. 4A except that the resonator 110c has two gap regions GR, and the conductive pattern 11 has two arc shapes facing each other.

Figure 4C:
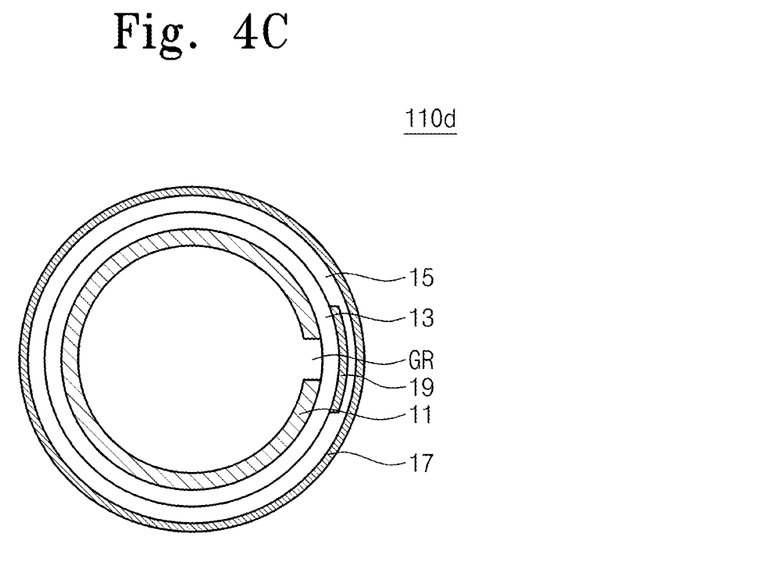

Referring to FIG. 4C, the resonator 110d of the current embodiment may further include one bridge electrode 19 adjacent to the gap region GR and disposed between the quartz tube 13 and the low-loss filler 15 in the same structure as the resonator 110b of FIG. 4A. The bridge electrode 19 may realize capacitance greater than that due to the gap region GR. Thus, the electric field in the resonator 110c may be almost zero to reduce the dielectric loss. Therefore, the measurement sensitivity may be improved. Here, the resonator 110d may have the same constitution as the resonator 110b of FIG. 4A except for the bridge electrode 19.

Figure 4D:
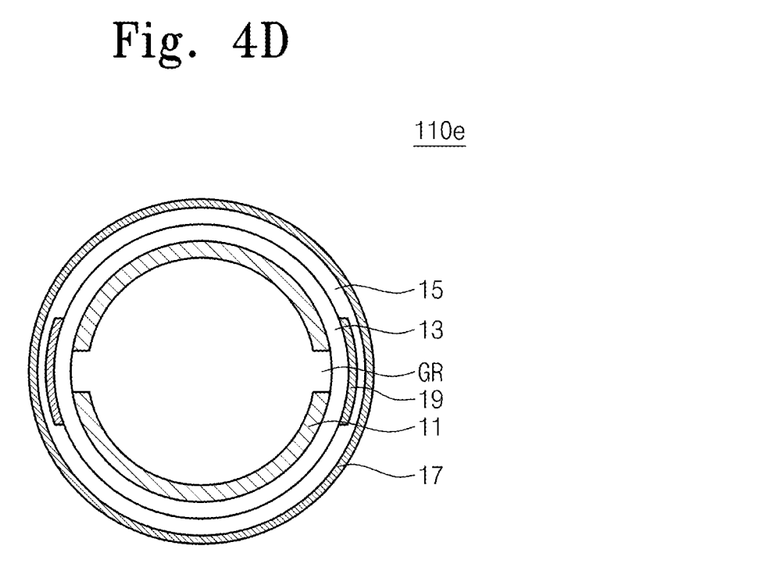

Referring to FIG. 4D, the resonator 110e of the current embodiment may further include two bridge electrodes 19 respectively adjacent to two gap regions GR in the same structure of as the resonator 110c of FIG. 4B. Here, the resonator 110e may have the same constitution as the resonator 110d of FIG. 4C except for the two bridge electrodes 19.

Each of the number of gap regions and the number of bridge electrodes may be at least three.

Although not shown, each of the resonators 110a to 110e according to the present invention may further include a coupler (or an antenna) inside the conductive pattern 11. Alternatively, the conductive pattern itself may function as the coupler. The coupler may be an arc-shaped conductive pattern having at least one gap region.

Figure 5:
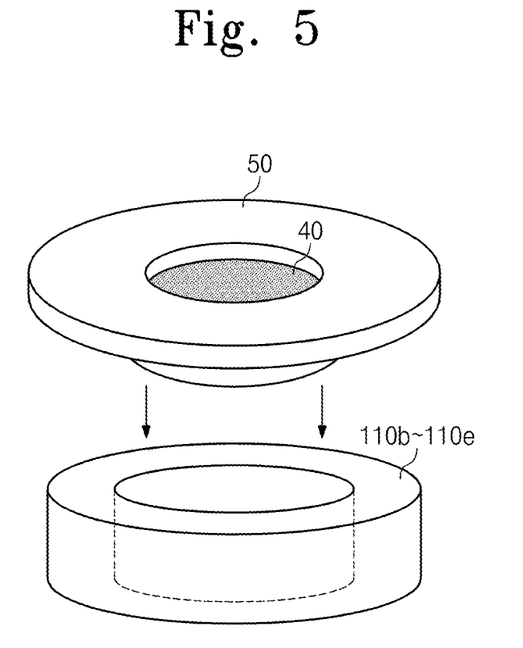
FIG. 5 is a view of a state a sample holder 50 is fitted into the resonator of FIGS. 4A to 4D.

FIG. 5 is a view of a state a sample holder 50 is fitted into the resonator of FIGS. 4A to 4D.

Referring to FIG. 5, the sample holder 50 filled with the sample 40 may be put into each of the resonators 110d to 110e. Here, the sample holder 50 may be filled with the sample 40. Then, as described with reference to FIG. 1, the measurement process may be progressed.

The resonator according to the present invention may include at least one gap region to improve the capacitance and change the intensity and shape of the electric field to improve the sensitivity. According to the present invention, the resonator may have the flat plate shape to increase the filling factor of the sample, thereby improving the measurement sensitivity. Also, the resonator may be miniaturized, and thus, the biosensor system including the resonator may also be miniaturized.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A resonator comprising:
   a conductor including an arc part, which has a C shape, and outer parts, which respectively extend outward from both ends of the arc part, such that the conductor has an omega shape as a whole;
   a dielectric substrate disposed below the conductor; and
   a high-dielectric pattern disposed between the outer parts of the conductor,
   wherein the high-dielectric pattern has a relative permittivity greater than a relative permittivity of the dielectric substrate.

2. The resonator of claim 1, wherein the high-dielectric pattern has the relative permittivity of about 10 or more.

3. The resonator of claim 1, wherein the dielectric substrate has the relative permittivity of about 6 or less.

4. The resonator of claim 1, wherein the conductor has a thickness of about 100 μm or less.

5. The resonator of claim 1, wherein the resonator has a flat plate shape and comprises a plurality of materials having different permittivities.

6. A biosensor system comprising:
   two electromagnets spaced apart from each other;
   a resonator disposed between the electromagnets to receive electrostatic fields from the electromagnets;
   a microwave bridge emitting microwave electric fields into the resonator;

a microwave detector detecting microwave energy reflected from the resonator;

a sample holder disposed within the resonator; and a biological sample disposed in the sample holder and including a magnetic bead, wherein the resonator comprises a conductor comprising at least one gap region.

7. The biosensor system of claim 6, wherein the sample holder is filled with the biological sample.

8. The biosensor system of claim 6, wherein the conductor has an arc part having the one gap region, or two arc parts, which are symmetrical to each other and have first and second gap regions therebetween.

9. The biosensor system of claim 8, wherein the resonator further comprises:

a circular quartz tube contacting an outer side of the conductor;

a low-loss filler surrounding an outer wall of the quartz tube; and a microwave shielding film surrounding an outer wall of the low-loss filler.

10. The biosensor system of claim 9, further comprising a bridge electrode adjacent to the gap region and disposed between the quartz tube and the low-loss filler.

11. The biosensor system of claim 6, wherein the conductor includes an arc part, which has a C shape, and outer parts, which respectively extend outward from both ends of the arc part such that the conductor has an omega shape as a whole, wherein the resonator further comprises:

a dielectric substrate disposed below the conductor; and a high-dielectric pattern disposed between the outer parts of the conductor, and wherein the high-dielectric pattern has a relative permittivity greater than a relative permittivity of the dielectric substrate.

12. The biosensor system of claim 11, wherein the high-dielectric pattern has the relative permittivity of about 10 or more.

13. The biosensor system of claim 11, wherein the dielectric substrate has the relative permittivity of about 6 or less.

14. A biosensor system comprising:

a resonator including:

a dielectric substrate;

a conductor disposed over the dielectric substrate and including an arc part that has a C shape and outer parts that respectively extend outward from both ends of the arc part such that the conductor has an omega shape as a whole; and a high-dielectric pattern disposed between the outer parts of the conductor, the high-dielectric pattern having a relative permittivity greater than a relative permittivity of the dielectric substrate; and a sample holder disposed within the resonator.

15. The biosensor system of claim 14, further comprising a biological sample disposed in the sample holder, the biological sample including a magnetic bead.

* * * * *